United States Patent [19]

Miura et al.

[11] Patent Number: 4,814,488

[45] Date of Patent: Mar. 21, 1989

[54] 4,4-BIS(4-HYDROXYPHENYL)CYCLOHEX-ANECARBOXYLIC ACID DERIVATIVES AND PROCESS FOR PREPARING SAME

[75] Inventors: Tohru Miura; Teruyuki Nagata, both of Omuta, Japan

[73] Assignee: Mitsui Toatsu Chemicals, Incorporated, Tokyo, Japan

[21] Appl. No.: 111,648

[22] Filed: Oct. 23, 1987

Related U.S. Application Data

[63] Continuation of Ser. No. 24,067, Mar. 12, 1987.

[30] Foreign Application Priority Data

Mar. 18, 1986 [JP] Japan ................................. 61-58405

[51] Int. Cl.$^4$ ............................................. C07C 69/76
[52] U.S. Cl. ................................................... 560/59
[58] Field of Search ........................................ 560/59

[56] References Cited

U.S. PATENT DOCUMENTS 4,537,704  8/1985  Sprecker et al. .................... 252/522

OTHER PUBLICATIONS

Journal of American Chemical Society, 58, 1738 (1936).
Bulletin of the Chemical Society of Japan, 30, 508–13 (1957).
Methoden der organischen Chemie, vol. 6/1c, No. 2, (1976), p. 1028.

*Primary Examiner*—Paul J. Killos
*Attorney, Agent, or Firm*—Fisher, Christen & Sabol

[57] ABSTRACT

Novel 4,4-bis(4-hydroxyphenyl)cyclohexanecarboxylic acid derivatives. These compounds can be prepared by reacting a cyclohexanone-4-carboxylic acid with a phenol.

7 Claims, 2 Drawing Sheets

4,4-BIS(4-HYDROXYPHENYL)CYCLOHEXANECARBOXYLIC ACID DERIVATIVES AND PROCESS FOR PREPARING SAME

This is a continuation of application Ser. No. 024,067, filed on Mar. 12, 1987.

BACKGROUND OF THE INVENTION a. Field of the Invention

This invention relates to novel 4,4-bis(4-hydroxyphenyl)cyclohexanecarboxylic acid derivatives and a process for preparing the same.

b. Description of the Prior Art 1,1-Bis(4-hydroxyphenyl)cyclohexane and its derivative having one or more alkyl groups on the cyclohexane ring, such as 4-methyl-1,1-bis(4hydroxyphenyl)cyclohexane, are well-known. For example, 1,1-bis(4-hydroxyphenyl)cyclohexane is a crystalline substance having a melting point of 184° C., while 4-methyl-1,1-bis(4-hydroxyphenyl)cyclohexane and 3,5-dimethyl-1,1-bis(4-hydroxyphenyl)cyclohexane are crystalline substances having melting points of 180° C. and 174° C., respectively (Methoden der organischen Chemie, Vol. 6, No. 2, 1028).

SUMMARY OF THE INVENTION

It is an object of the present invention to provide novel 4,4-bis(4-hydroxyphenyl)cyclohexanecarboxylic acid derivatives.

It is another object of the present invention to provide a process for preparing novel 4,4-bis(4-hydroxyphenyl)cyclohexanecarboxylic acid derivatives.

The 4,4-bis(4-hydroxyphenyl)cyclohexanecarboxylic acid derivatives of the present invention can be represented by the formula

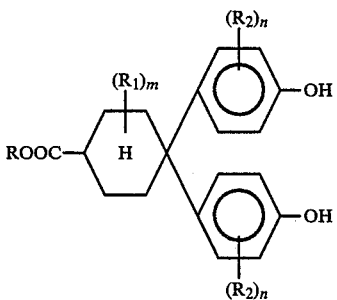

where R is a hydrogen atom or a lower alkyl group, $R_1$ and $R_2$ are lower alkyl groups, and m and n are whole numbers of 0 to 4.

The compounds of the present invention are useful as precursors of 4-hydroxybiphenyl-4'-carboxylic acids which are very useful as starting materials for the synthesis of polymers and the like. The conversion of these compounds into 4-hydroxybiphenyl-4'-carboxylic acids is described in our copending Japanese patent applications No. 76684/1986 filed Apr. 4, 1986; No. 158707/1986 filed July 8, 1986; and No. 223889/1986 filed Sept. 24, 1986. These applications correspond to U.S. Ser. No. 031,709, filed on Mar. 30, 1987.

The compounds represented by the formula (I) can be prepared by reacting a cyclohexanone-4-carboxylic acid of the formula

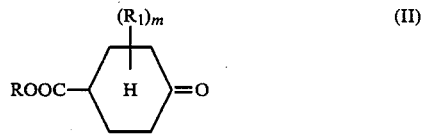

where R, $R_1$ and m are as defined for formula (I), with a phenol of the formula

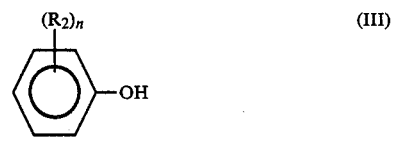

where $R_2$ and n are as defined for formula (I).

BRIEF DESCRIPTION OF THE DRAWING

In the accompanying drawing

DETAILED DESCRIPTION OF THE INVENTION

Figure 1:
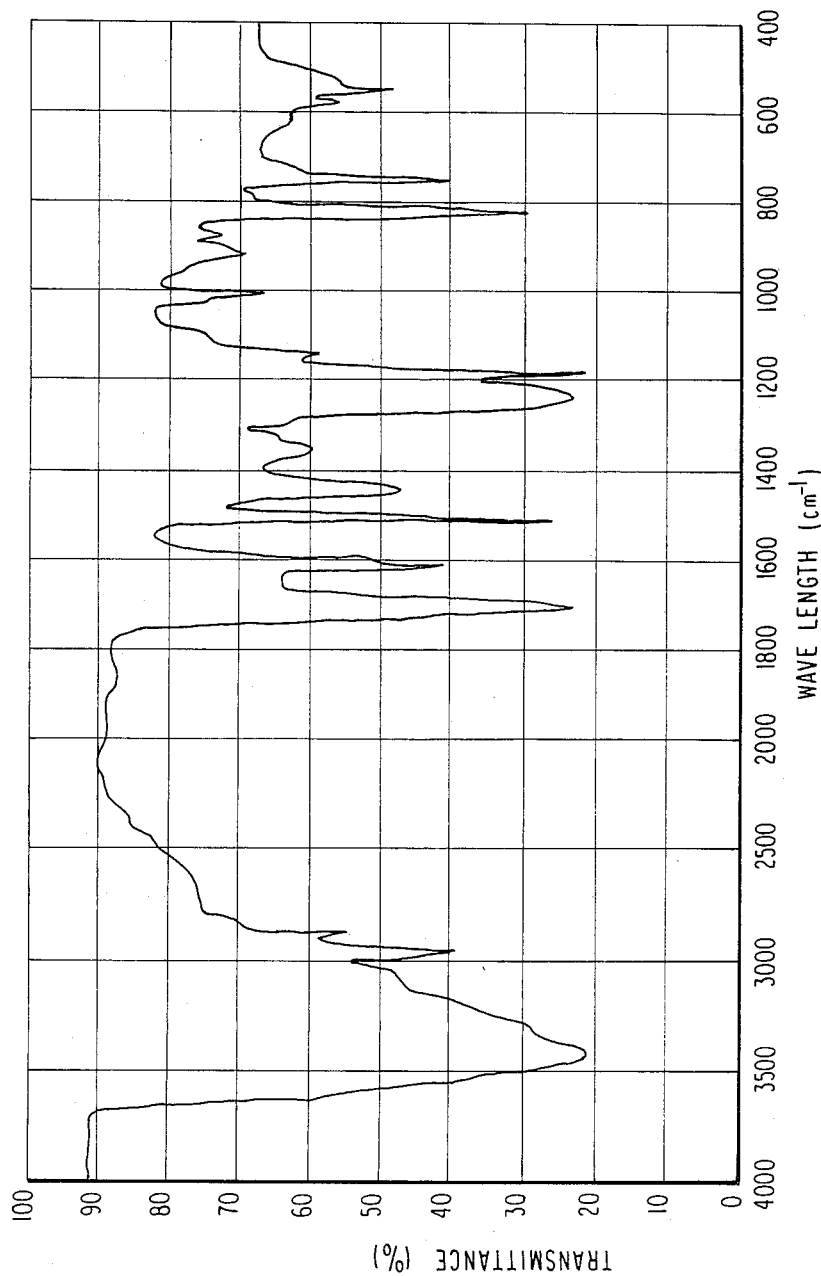
FIG. 1 is the infrared spectrum of 4,4-bis(4-hydroxyphenyl)cyclohexanecarboxylic acid obtained in Example 1.

Specific examples of the compounds of formula (I) include 4,4-bis(4-hydroxyphenyl)cyclohexanecarboxylic acid, the methyl, ethyl and butyl esters of 4,4-bis(4-hydroxyphenyl)cyclohexanecarboxylic acid, 4,4-bis(3,5-dimethyl-4-hydroxyphenyl)cyclohexanecarboxylic acid methyl ester, 4,4-bis(3-tert-butyl-4-hydroxyphenyl) cyclohexanecarboxylic acid and 4,4-bis(4-hydroxyphenyl)2-methylcyclohexanecarboxylic acid methyl ester.

Preferably, the lower alkyl groups represented by R, $R_1$ and $R_2$ in the above formula (I) are alkyl groups having 1 to 4 carbon atoms.

The reaction of a cyclohexanone-4-carboxylic acid of formula (II) with a phenol of formula (III) is preferably carried out in the presence of an acid catalyst. Examples of the acid catalyst used for this purpose include hydrogen chloride gas, hydrochloric acid, sulfuric acid, phosphoric acid, toluenesulfonic acid, $BF_3$, $ZnCl_2$, $AlCl_3$, $SnCl_4$, cation exchange resins having movable acid groups, and the like. These catalysts may be used in an amount of 0.1 to 30 parts by weight per 100 parts by weight of the cyclohexanone4-carboxylic acid of formula (II).

Moreover, the reaction rate can further be enhanced by the additon of a co-catalyst. Active co-catalysts include alkyl mercaptans such as methyl mercaptan, ethyl mercaptan, n-propyl mercaptan, isopropyl mercaptan, n-butyl mercaptan, isobutyl mercaptan, tert-butyl mercaptan, etc., as well as high-molecular-weight alkyl mercaptans. It is also possible to use other sulfur compounds such as hydrogen sulfide, thiophenol, thioalcohols, thio acids, polymeric thioacetone, dialkyl sulfides, etc., as well as analogous selenium compounds.

The aforesaid reaction may be carried out in a solvent which exerts no adverse influence on the reaction, and usable solvents include aromatic hydrocarbons, chlorinated aliphatic hydrocarbons, glacial acetic acid and the like. However, in order to enhance the yield of the product and minimize the occurrence of said reactions, it is desirable to use an excess of the phenol as the solvent. The amount of phenol used is suitably in the range of 2 to 10 parts by weight per part by weight of the cyclohexanone-4-carboxylic acid.

In the process of the present invention, the reaction is carried out at a temperature of 30 to 100° C. and preferably 40 to 70° C. If the reaction temperature is too high, the formation of by-products will undesirably increase and, therefore, cause a reduction in the yield of the product.

The 4,4-bis(4-hydroxyphenyl)cyclohexane carboxylic acid derivative formed as a result of the reaction can be isolated by pouring the reaction mass into a solvent (such as benzene or the like) in which the compounds of the present invention are hardly soluble, and then cooling the resulting mixture to crystallize the product.

The phenol used in excess can be recovered and re-used by neutralizing the mother liquor and filtering off the crystallized salts, or by distilling the mother liquor under reduced pressure.

The cyclohexanone-4-carboxylic acids serving as starting materials in the process of the present invention can be obtained by reacting the corresponding 4-hydroxybenzoic acids (such as 4-hydroxybenzoic acid, methyl 4-hydroxybenzoate, ethyl 4-hydroxybenzoate, propyl 4-hydroxybenzoate and butyl 4-hydroxybenzoate) in a solvent (such as water, acetic acid, alcohols, etc.) under the influence of a catalyst comprising, for example, palladium supported on a carrier.

The present invention is further illustrated by the following examples. However, these examples are given merely by way of illustration and are not to be construed to limit the scope of the invention.

EXAMPLE 1

Preparation of cyclohexanone-4-carboxylic acid

One mole of 4-hydroxybenzoic acid was reacted with two moles of hydrogen in the presence of 5% palladium-carbon catalyst. This reaction was carried out in isopropyl alcohol at a temperature of 130°–140° C. and a hydrogen pressure of 20–40 kg/cm² (gauge) After the reaction mixture was filtered to recover the catalyst therefrom, the filtrate was distilled to recover the solvent. The resulting residue was recrystallized from a mixture of benzene and hexane to obtain cyclohexane-4-carboxylic acid. This product had a melting point of 67.0°–68.0° C.

Preparation of 4,4-bis(4-hydroxyphenyl)cyclohexanecarboxylic acid

Into a 500-ml reaction flask were charged 35.5 g of cyclohexanone-4-carboxylic acid, 284.0 g of phenol and 30 ml of 36% hydrochloric acid. This reaction mixture was stirred at 40°–45° C. for 6 hours. After completion of the reaction, hydrogen chloride-containing water was removed by means of an evaporator. Thereafter, the greater part of phenol was removed by distillation and the remaining phenol was then removed by sludging with 300 ml of benzene. The precipitate so formed was collected by filtration and then dried to obtain 74.9 g of white crystals. By subjecting these crystals to column chromatography, there was obtained a pure crystalline product which was identified as 4,4-bis(4 hydroxyphenyl)cyclohexanecarboxylic acid on the basis of its ¹H-NMR and infrared spectra. The crude crystals were obtained in a 94% yield and had a purity of 98%.

The ¹H-NMR data of 4,4-bis(4-hydroxyphenyl)cyclohexanecarboxylic acid are shown in Table 1. In addition, its infrared spectrum is shown in FIG. 1.

TABLE 1

| Signal | ppm | Assignment |
|---|---|---|
| a | 1.3–2.1 | Cyclohexane ring |
| b | 2.1–2.6 | |
| c | 6.5–6.8 | p-Substituted benzene |
| d | 6.9–7.2 | |
| e | 8.2 | —COOH |
| f | 8.8–9.4 | —OH |

Each peak area coincided with the corresponding proton ratio.

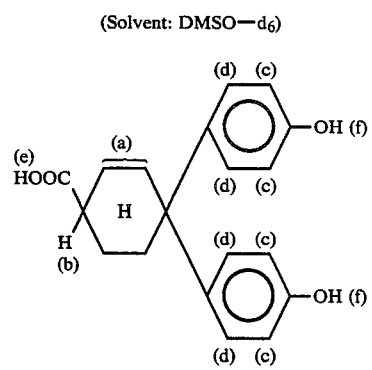

(Solvent: DMSO—d₆)

EXAMPLE 2

Preparation of cyclohexanone-4-carboxylic acid methyl ester

One mole of methyl 4-hydroxybenzoate was reacted with two moles of hydrogen in the presence of 5% palladiun-carbon catalyst. This reaction was carried out in isoproyl alcohol at a temperature of 170°–180° C. and a hydrogen pressure of 20–40 kg/cm². After the reaction mixture was filtered to recover the catalyst therefrom, the filtrate was distilled to obtain cyclohexanone-4-carboxylic acid methyl ester as the distillate at 140° C./20 mmHg.

Preparation of 4,4-bis(4-hydroxyphenyl)cyclohexanecarboxylic acid methyl ester Into a 300-ml reaction flask were charged 62.5 g (0.40 mole) of cyclohexanone-4-carboxylic acid methyl ester, 188.2 g (2.0 moles) of phenol and 20 ml of 36% hydrochloric acid. This reaction mixture was stirred at 40°–45° C. for 5 hours. After completion of the reaction, the reaction mixture was poured into 500 ml of benzene, followed by stirring at 20° C. for 1 hour. The precipitate so formed was collected by filtration and then dried to obtain 103.7 g of white crystals. By subjecting these crystals to column chromatography, there was obtained a pure crystalline product which was identified as 4,4-bis(4-hydroxyphenyl)cyclohexanecarboxylic acid methyl ester on the basis of its ¹H-NMR and infrared spectra. The crude crystals were obtained in a 65% yield and had a purity of 82%, and the greater part of the by-products comprised 4,4-bis(4-hydroxyphenyl)- cyclohexanecarboxylic acid formed as a result of hydrolysis.

Figure 2:
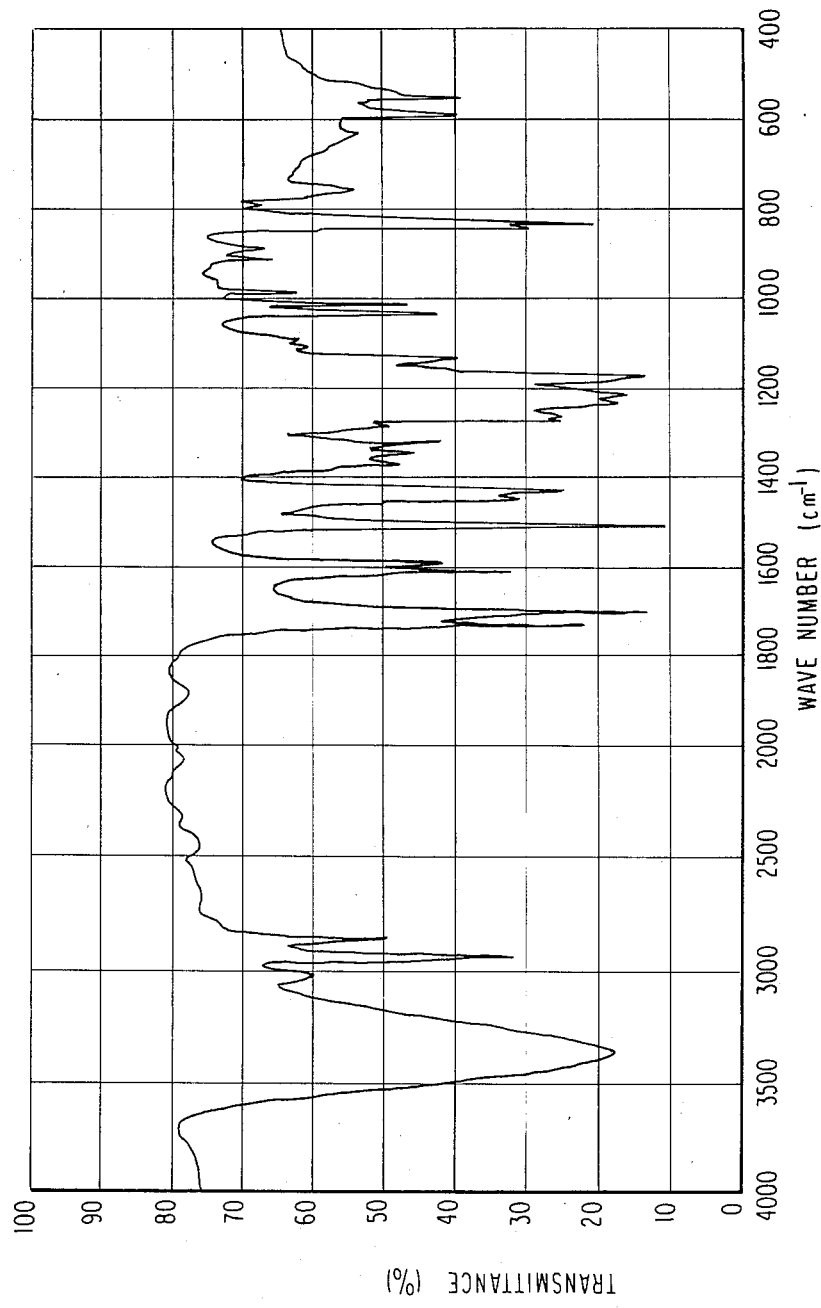
FIG. 2 is the infrared spectrum of 4,4-bis( 4-hydroxypheny)cyclohexanecarboxylic acid methyl ester obtained in Example 2.

The $^1$H-NMR data of 4,4-bis(4-hydroxyphenyl)cyclohexanecarboxylic acid methyl ester are shown in Table 2. In addition, its infrared spectrum is shown in FIG. 2.

TABLE 2

| Signal | ppm | Assignment |
| --- | --- | --- |
| a | } 1.4–2.0 | Cyclohexane ring |
| b | | |
| c | 3.5 | —COOCH$_3$ |
| d | 6.5–6.7 | } p-Substituted benzene |
| e | 6.9–7.2 | |
| f | 8.8–9.0 | —OH |

Each peak area coincided with the corresponding proton ratio.

(Solvent: DMSO—d$_6$)

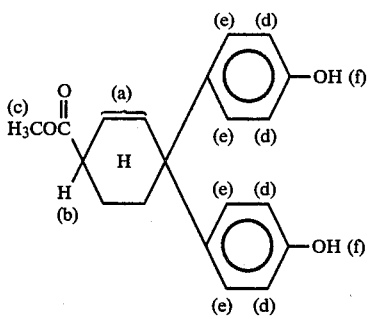

EXAMPLE 3

The procedure of Example 2 for the preparation of cyclohexanone-4-carboxylic acid methyl ester was repeated, except that the starting methyl 4-hydroxy-benzoate was replaced by ethyl 4-hydroxybenzoate. Thus, there was obtained cyclohexanone-4-carboxylic acid ethyl ester (B.P. 150°–152° C./40 mmHg; n$^{D25}$=1.4594).

In the same manner as described in Example 2, this compound was reacted with phenol to obtain a white crystalline product.

On the basis of its NMR and infrared spectra, this product was identified as 4,4-bis(4-hydroxyphenyl)cyclohexanecarboxylic acid ethyl ester.

EXAMPLE 4

Into a reaction flask were charged 62.5 g (0.40 mole) of cyclohexanone-4-carboxylic acid methyl ester, 244.3 g (2.0 moles) of 2,6-xylenol, 6.3 g of n-butyl mercaptan and 200 ml of toluene. While this mixture was kept at 40°–45° C., reaction was effected by blowing hydrogen chloride gas therethrough for 8 hours at a rate of 2–10 ml/min. After completion of the reaction, the reaction mixture was cooled by the addition of 200 ml of toluene and 100 ml of water, and then sludged at room temperature for 30 minutes. The precipitate so formed was collected by filtration, washed with toluene, and then dried to obtain 140.3 g of white crystals. After purification, this prdduct was identified as 4,4-bis(3,5-dimethyl-4-hydroxyphenyl) cyclohexanecarboxylic acid methyl ester on the basis of its NMR and infrared spectra. The crude crystals were obtained in a 66% yield and had a purity of 72%.

EXAMPLE 5

Into a reaction flask were charged 56.9 g (0.40 mole) of cyclohexanone-4-carboxylic acid, 480.7 g (3.2 moles) of o-tert-butylphenol and 5.7 g of n-butyl mercaptan. While this mixture was kept at 60° C., reaction was effected by blowing hydrogen chloride gas therethrough for 6 hours at a rate of 2–10 ml/min. After completion of the reaction, the reaction mixture was poured into a two-layered mixture consisting of 500 ml of toluene and 100 ml of water, followed by sludging at room temperature for 30 minutes. The precipitate so formed was collected by filtration, washed with toluene, and then dried to obtain 159.1 g of white crystals. After purification, this product was identified as 4,4-bis(3-tert-butyl-4-hydroxyphenyl)cyclohexanecarboxylic acid on the basis of its NMR and infrared spectra. The crude crystals were obtained in an 88% yield and had a purity of 95%.

EXAMPLE 6

Preparation of 3-methylcyclohexanone-4-carboxylic acid methyl ester

2-Methyl-4-hydroxybenzoic acid was heated in methanol under the influence of sulfuric acid catalyst to convert it into its methyl ester. One mole of the methyl 2-methyl-4-hydroxybenzoate thus obtained was reacted with two moles of hydrogen in the presence of palladium-carbon catalyst. This reaction was carried out in isopropyl alcohol at a temperature of 150°–170° C. and a hydrogen pressure of 20–40 kg/cm$^2$. After the reaction mixture was filtered to recover the catalyst therefrom, the filtrate was distilled to obtain 3-methylcyclohexanone-4-carboxylic acid methyl ester as the distillate at 112°–120° C./5 mmHg.

Preparation of 4,4-bis(4-hydroxyphenyl)-2-methylcyclohexhecarboxylic acid methyl ester Into a 300-ml reaction flask were charged 68.1 g of 3-methylcyclohexanone-4-carboxylic acid methyl ester, 187.5 g of phenol and 20 ml of 36% hydrochloric acid. This reaction mixture was stirred at 40°–45° C. for 6 hours. After completion of the reaction, the reaction mixture was worked up in the same manner as described in Example 2. Thus, there was obtained 112.9 g of white crystals. After purification, this product was identified as 4,4-bis(4-hydroxyphenyl)-2-methylcyclohexanecarboxylic acid methyl ester on the basis of its NMR and infrared spectra. The crude crystals were obtained in a 63% yield and had a purity of 76%.

What is claimed is:

1. A process for preparing 4,4-bis(4-hydroxyphenyl)cyclohexanecarboxylic acid derivatives which comprises reacting a cyclohexanone-4-carboxylic acid of the formula:

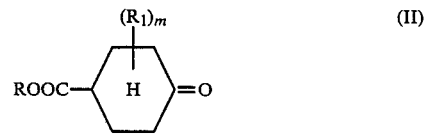

wherein R is a hydrogen atom or a lower alkyl group, R₁ is a lower alkyl group and m is a whole number 0 to 4, with a phenol of the formula:

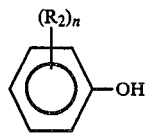 (III)

wherein R₂ is a lower alkyl group and n is a whole number 0 to 4.

2. A process as claimed in claim 1 wherein the reaction is carried out in the presence of an acid catalyst.

3. A process as claimed in claim 2 wherein the acid catalyst is hydrogen chloride, hydrochloric acid, sulfuric acid, phosphoric acid, toluenesulfonic acid, boron trifluorine, zinc chloride, aluminum chloride, stannic chloride or a cationic exchange resin.

4. A process as claimed in claim 2 wherein the acid catalyst is used in an amount of 0.1 to 30% by weight based on the cyclohexanone-4-carboxylic acid.

5. A process as claimed in claim 2 wherein a co-catalyst is used in combination with the acid catalyst.

6. A process as claimed in claim 1 wherein the phenol is used in an amount of 2 to 10 parts by weight per part by weight of the cyclohexanone-4-carboxylic acid.

7. A process as claimed in claim 1 wherein the reaction is carried out at a temperature of 30° to 100° C.

* * * * *